(12) United States Patent
Burat et al.

(10) Patent No.: US 7,735,370 B2
(45) Date of Patent: Jun. 15, 2010

(54) METHOD FOR TESTING THE CONDITION OF A DRIVE SHAFT OF A ROTARY MACHINE

(75) Inventors: Olivier Pierre Burat, Givry (FR); Jean Joseph Cavalier, Maubeuge (FR)

(73) Assignee: JSPM, Jeumont (FR)

( * ) Notice: Subject to any disclaimer, the term of this patent is extended or adjusted under 35 U.S.C. 154(b) by 393 days.

(21) Appl. No.: 11/921,290

(22) PCT Filed: May 31, 2006

(86) PCT No.: PCT/FR2006/001245

§ 371 (c)(1),
(2), (4) Date: Nov. 29, 2007

(87) PCT Pub. No.: WO2006/129019

PCT Pub. Date: Dec. 7, 2006

(65) Prior Publication Data

US 2009/0320599 A1    Dec. 31, 2009

(30) Foreign Application Priority Data

Jun. 1, 2005    (FR) .................................. 05 51459

(51) Int. Cl.
*G01B 11/16* (2006.01)

(52) U.S. Cl. .............................. 73/660; 73/593; 73/596; 73/633; 73/649

(58) Field of Classification Search .................. 73/660, 73/593, 596, 602, 618, 619, 620, 622, 626, 73/633, 649
See application file for complete search history.

(56) References Cited

U.S. PATENT DOCUMENTS

| | | | | |
|---|---|---|---|---|
| 4,462,255 A | * | 7/1984 | Guess et al. ................... | 73/633 |
| 4,497,210 A | | 2/1985 | Uchida et al. ................. | 73/602 |
| 4,677,981 A | * | 7/1987 | Coursant ..................... | 600/447 |
| 5,113,697 A | * | 5/1992 | Schlawne ..................... | 73/602 |
| 5,431,053 A | * | 7/1995 | Fink ............................ | 73/602 |
| 5,670,779 A | * | 9/1997 | Bell ....................... | 250/231.13 |
| 5,932,807 A | * | 8/1999 | Mallart ........................ | 73/641 |
| 6,144,483 A | * | 11/2000 | Allen et al. ................. | 359/305 |
| 6,749,569 B1 | * | 6/2004 | Pellegretti ................... | 600/441 |
| 6,996,480 B2 | * | 2/2006 | Giurgiutiu et al. ............ | 702/35 |

(Continued)

FOREIGN PATENT DOCUMENTS

JP    2004 340809    12/2004

*Primary Examiner*—J M Saint Surin
(74) *Attorney, Agent, or Firm*—Davidson, Davidson & Kappel, LLC (57) ABSTRACT

A method for non-destructive testing of a drive shaft that is accessible by only one of its ends in longitudinal waves, using a multi-element annular ultrasonic transducer. Such a transducer consists of independent elements that can be excited by electrical pulses of the same frequency, but for which different electronic phase shifts will be applied, in the invention, to the pulses transmitted to the elements. Such an electronic phase shift allows the focussing or deflection of a final beam synthesized by all the elements constituting the transducer, the said final beam being concentrated to adopt a generally cylindrical shape with a cross-section that is far smaller than the cross-section of the shaft to be tested and is highly energetic over a long distance due to the waveguide effect created by the cylindrical geometry of the shaft.

12 Claims, 6 Drawing Sheets

U.S. PATENT DOCUMENTS 7,428,842 B2 * 9/2008 Fair et al. .................... 73/626
7,429,352 B2 * 9/2008 Bisiaux et al. ............... 266/99
2002/0113974 A1 * 8/2002 Clark ........................ 356/519

* cited by examiner

PRIOR ART

Fig. 3

PRIOR ART

Fig. 4

PRIOR ART

METHOD FOR TESTING THE CONDITION OF A DRIVE SHAFT OF A ROTARY MACHINE

This invention relates to a method for controlling the condition of a drive shaft of a rotary machine. Its object is essentially to propose a solution for carrying out a non-destructive test for the condition of a drive shaft, one end of which is accessible for carrying out the said test.

The invention will be described in greater detail with reference to a primary nuclear reactor pump, the said primary pump comprising in particular a wheel driven by an electric motor through a drive shaft to be tested. However, the method according to the invention may be used to test the condition of any solid shaft, particularly carbon steel or stainless steel shafts used in a rotary machine subject to thermal, mechanical or other stresses that are likely to damage the said shaft.

BACKGROUND

The field in which the use of the method according to the invention will be described in great detail is that of primary pumps of a nuclear reactor cooled by water under pressure. An example of such a pump currently in use is described with reference to FIGS. 1 and 2.

Figure 1:
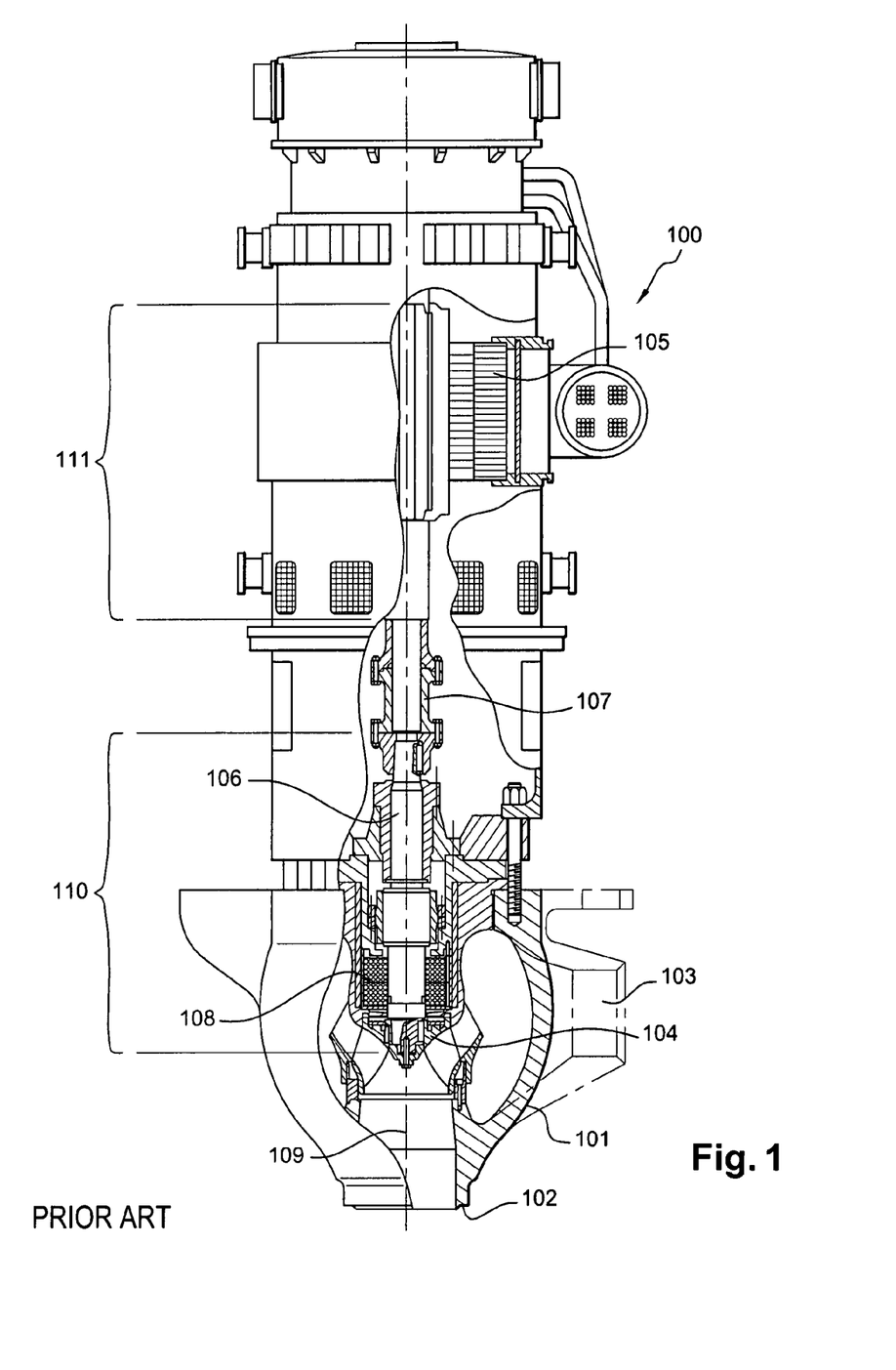
in FIG. 1, already described, a partial sectional view of a primary pump of a nuclear reactor with water under pressure, taking the example of a drive shaft intended to be tested by means of the method according to the invention.

FIG. 1 shows a pump 100—called a primary pump—normally used in nuclear reactors cooled by water under pressure; primary pump 100 serves to put into circulation, in the cooling circuit of the nuclear reactor, referred to as the primary circuit, the cooling water of the nuclear reactor under pressure. Pump 100 comprises, in particular:

a pump body 101, connected by means of a first tube 102 to a first pipe of the primary circuit, and by a second tube 103 to a second pipe of the nuclear reactor; pump 100 puts the water into circulation between these two tubes, establishing a certain pressure;

a wheel 104, driven by an electric motor 105;

a drive shaft 106, having a lower section 110, called a pup shaft, this lower section being itself capable of being considered as a drive shaft, secured to wheel 104, and an upper section, called the motor shaft, connected by means of a coupling 107, called the intermediate shaft, to the rotor of electric motor 105; drive shaft 106, more particularly pump shaft 110, is generally cylindrical, although it includes, in an axial direction 109, of a succession of sections slightly different in diameter, thereby allowing the installation and housing of different elements, in particular pump wheel 104 or a protective thermal ring; the differences in the existing diameter, however, are sufficiently low to qualify the drive shaft as a generally cylindrical shaft;

an assembly of means of cooling, rotary guidance of shaft 106 and sealing arranged on the periphery of drive shaft 106; these means include, in particular, a thermal barrier 108, including a network of tubes through which a cooling fluid passes, and arranged around a lower section of the lower end of pump shaft 110;

a plurality of assembly means, in particular positively connected keys 112 driven into a recess arranged in the lower section of pump shaft 110, or rotary fixing 113 or stop pins inserted in recesses arranged in the drive shaft at the point where thermal barrier 108 is located.

Figure 2:
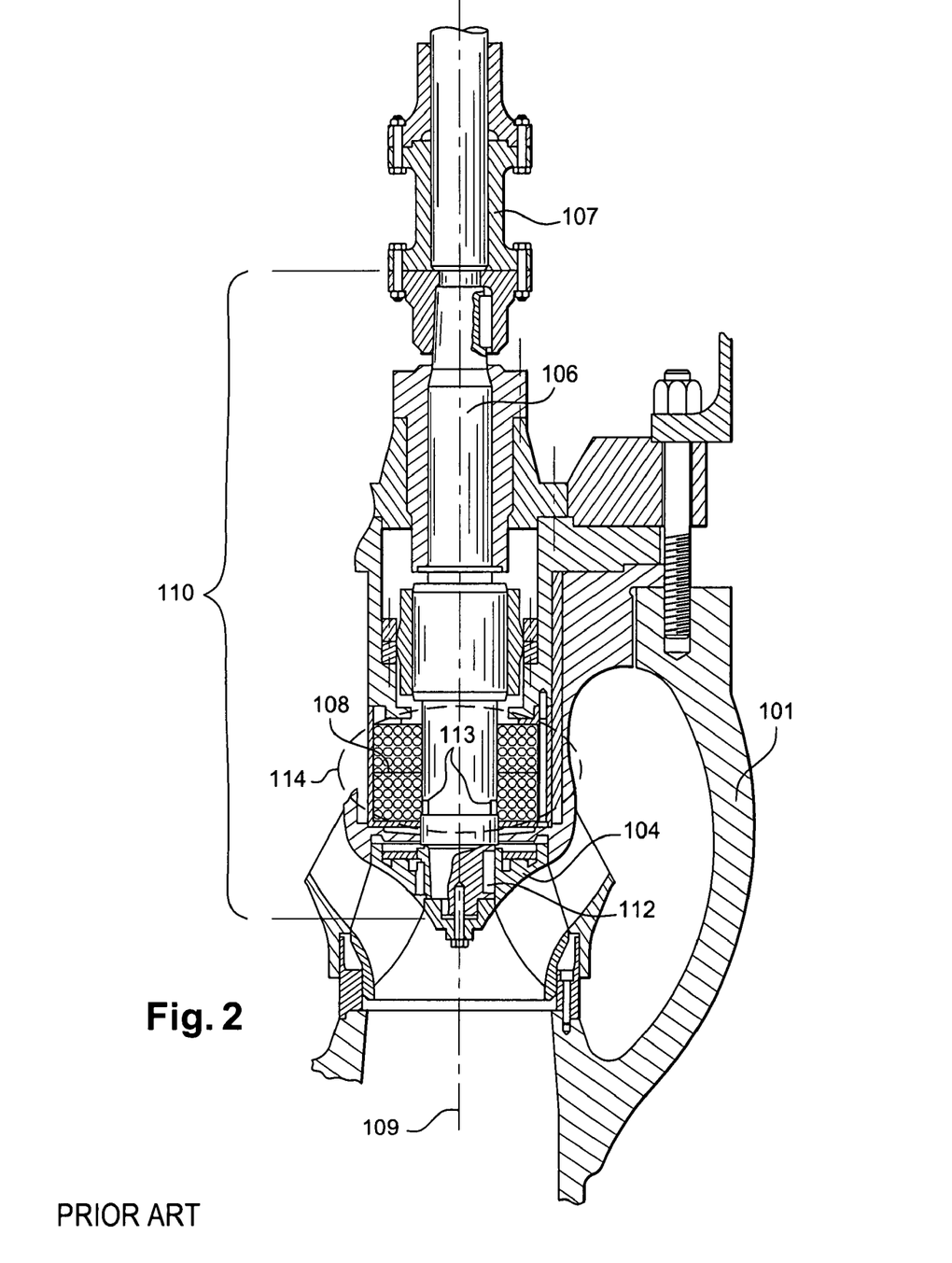
in FIG. 2, also already described, a larger scale sectional view of the drive shaft shown in FIG. 1.

The lower end of pump shaft 110 is caused to be immersed in water under pressure at a temperature of the order of 280° C. (degrees Celsius). Moreover, in normal operation, cold water, at a temperature lower than 55° C., is injected at thermal barrier 108 to form a barrage between the primary circuit and means of sealing the shaft. Under these conditions there is a transition zone 114 between the drive shaft and thermal barrier subject to major variations in temperature due to the mixture of water from the primary circuit at 280° C. and the injection water at 55° C.; the corresponding section of the shaft is therefore subject to major thermal stresses that are likely to result in the occurrence of cracks or a crazing phenomena in this section of the shaft, in if thermal rings are added. Cracks of thermal origin are multiple and form a network. The deepest cracks have a preferably axial orientation.

In addition to the cracks of thermal origin cracks of a mechanical origin are also observed: the latter appear either in the changes of cross-section or in the holes of stop pin 113 blocking the rotation of parts secured to drive shaft 106, or in the keyways, for example those of keys 112. They have a preferably transversal orientation. There are generally no multiple cracks, except where multiple pin holes are drilled. Moreover, drive shaft 106 is subject to risks of torsional fracture at the changes of cross-section found along the shaft.

Therefore the defects sought, whether they result from fatigue of mechanical or thermal origin, or even both, commence on the surface and spread progressively toward the inside of the part. They are mainly located in the lower section of the primary pump, a section subject to substantial temperature gradients.

In the state of the art different solutions have been proposed for detecting the occurrence of such defects in the lower section of pump shaft 110. In particular, several test methods have been proposed involving the use of ultrasonic transducers. Such transducers transmit ultrasonic beams in the shaft; these beams are reflected mainly at the location of the above-mentioned defects of the shaft; they are then received by the ultrasonic transducers that are coupled to an assembly of signal processing means for their interpretation and hence clearest possible detection of the existence and positioning of the said defects. In all the test methods there is an intermediate shaft that connects the pump shaft to the motor shaft, thereby providing access to an upper end of the pump shaft.

Figure 3:
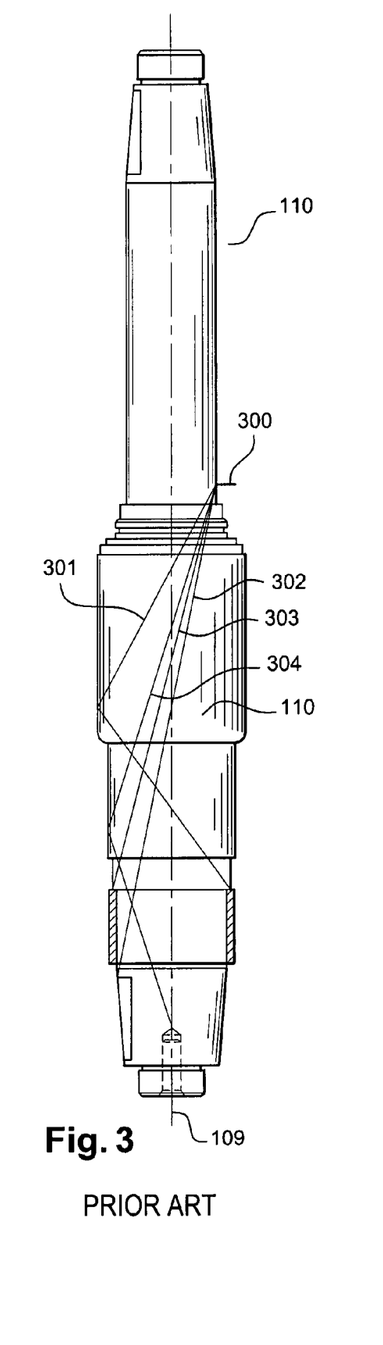
in FIG. 3, also already described, a diagrammatic representation of a first method of testing a drive shaft, according to the state of the art.

A first family of solutions resides in the use of transversal ultrasonic waves. Such an example of a solution is shown in FIG. 3, in which a drive shaft comparable to pump shaft 110 is tested. In this method an ultrasonic transducer—or sensor—is positioned at a gearing point 300, in contact with pump shaft 110; depending on the position of the sensor, different points to be tested may be reached, possibly after one or more reflections on the surface of the drive shaft, the beam being capable of taking different trajectories, different examples of which are denoted by references 301, 302, 303 and 304 respectively, so that each is able to reach a point to be tested. The sensors used are in most cases parallelepipedic mono-element transducers provided with a ferrule that enables the beam to deflect by an angle of up to approx. 75° to the axis of the shaft.

The advantage of this method is that it enables the defects to be located vertically and angularly: a rotary movement of the transducer about the drive shaft enables a circumference of the shaft, determined vertically by suitable axial positioning of the transducer, to be scanned. However, the transversal transducers must be used as close as possible to the zone to be tested; they must be arranged in positions that are lower than the directly accessible positions of the pump shaft; it is then necessary to dismantle the pump shaft, which complicates the test operation, particularly in the case of nuclear primary pumps. Such transducers also suffer from the disadvantaging of having a large beam opening, i.e. a low resolution, revealing only relatively major transversal defects. The axial defects arising from thermal fatigue are not detectable.

Moreover, it is necessary to use a ferrule for positioning the transducer in a given orientation, and hence obtain a desired angle of incidence, which complicates the test operation even more. Furthermore, the presence of thermal rings prevents the transducer from being positioned at the corresponding level of the shaft. Finally, it may be necessary, for testing the lowest points, to use several reflections of the ultrasonic beam, which involves a major loss of energy and thereby limiting the resolution of the return information. Therefore the longer the shaft the more difficult it is to apply the method.

A second family of solutions resides in the use of longitudinal waves. These test methods make use of transducers which transmit a divergent ultrasonic beam 400, shown in FIG. 4, whose width, at a great distance, i.e. at approximately three metres, is contained within the diameter of pump shaft 110. These solutions make use of transducers of the type with cylindrical mono-elements, annular mono-elements, or even annular transducers with two elements or with two groups of separate elements, with one element or a group of elements used for transmission, and one element or a group of elements used for reception.

Figure 4:
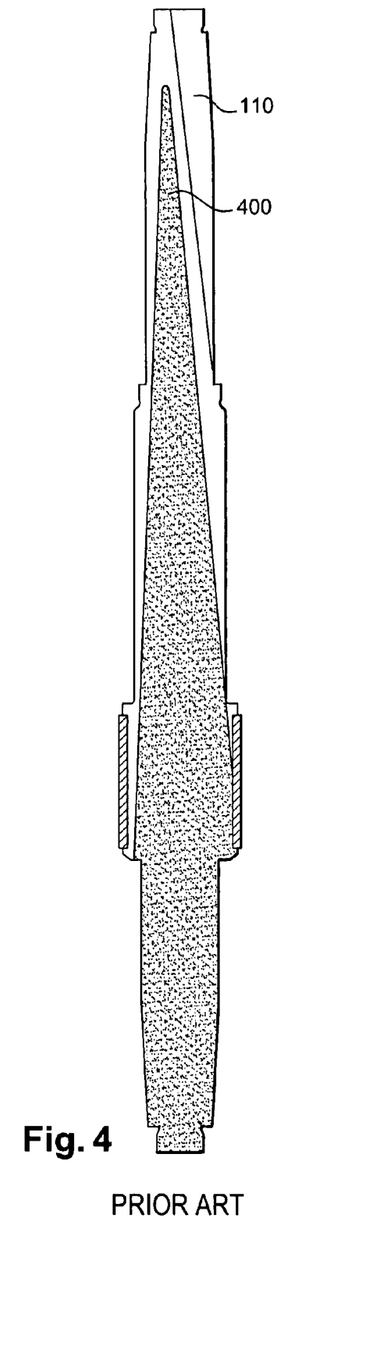
in FIG. 4, also already described, a diagrammatic representation of a second method of testing a drive shaft, according to the state of the art.

These tests allow the detection of large transversal defects and their location vertically in the shaft. However, it is not possible to position them precisely and angularly on the periphery of the shaft. Transversal cracks of a mechanical origin, with a small reflecting surface, are difficult to detect since the resolution is dependent on the ratio of the area of the defect to the area of the beam in the same plane.

Moreover, axial defects are not detectable since the energy transmitted is never sufficient to be diffracted in sufficient quantity to the transducers through the upper end of axial defects.

Testing with this type of transducer may be improved by adding acoustic lenses, which improve the resolution and location of defects on the periphery but which suffer from the disadvantage of having a given focus, corresponding to a single distance, which involves having as many sensors as different heights to be examined. Moreover, axial defects remain non-detectable by these improved transducers.

Finally it should be noted that the operation which has just been described corresponds to a theoretical principle of use inherent in the technology of ultrasonic transducers in homogeneous and isotropic environments. Now forged shafts, and in particular shafts in austenitic or austenoferritic stainless steel, which are present mainly in the primary pumps of nuclear reactors, have a heterogeneity zone 500, shown in FIG. 5, with a metallurgical structure; these heterogeneities are found mainly in the thickest sections, and they vary from one shaft to another according to chemical composition, the forging range and the range of heat treatments applied.

Figures 5, 6, 7, 8:
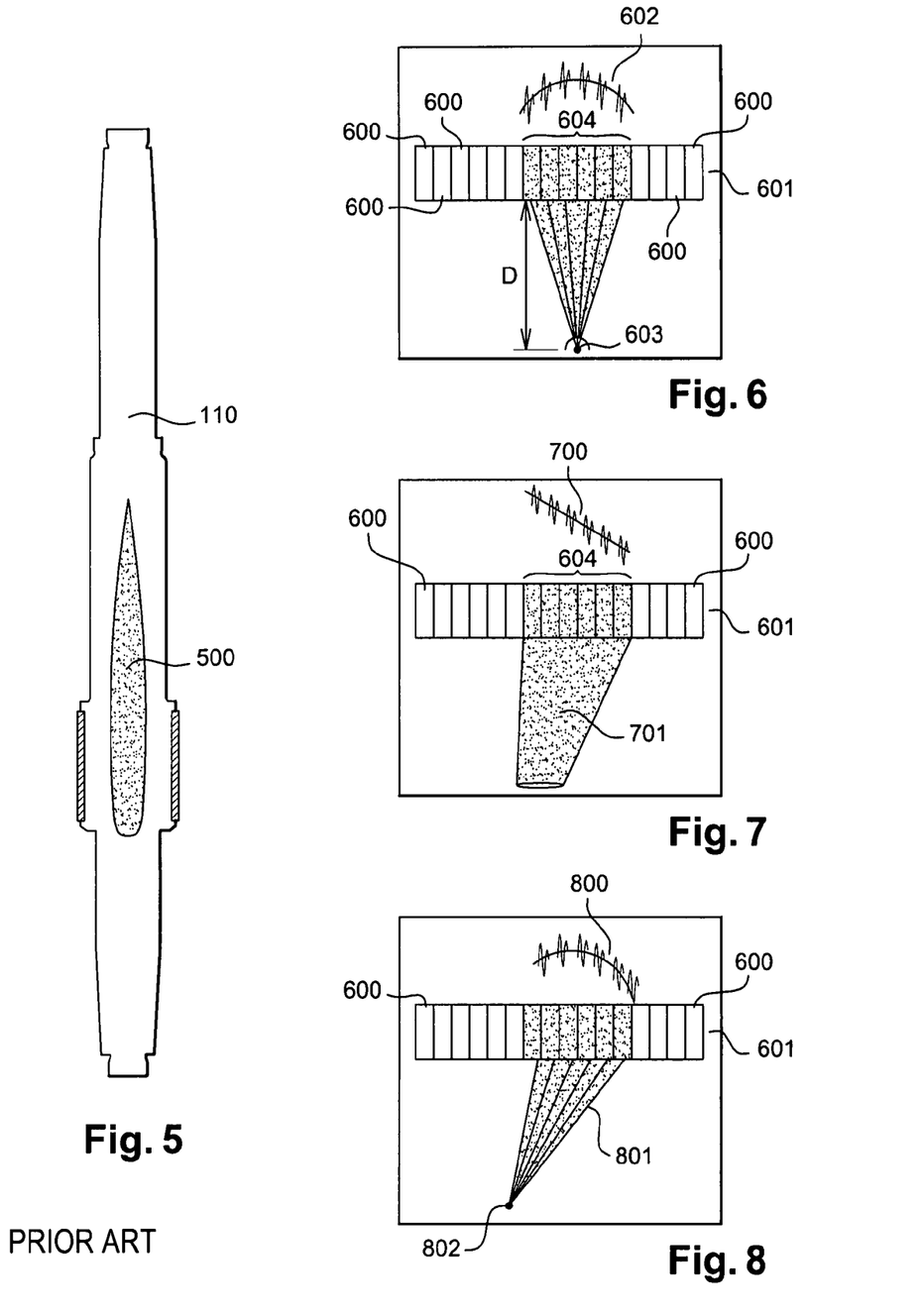
in FIG. 5, also already described, a diagrammatic representation of a drive shaft to be tested by means of the method according to the invention.
in FIG. 6, a diagrammatic illustration of the principle of electronic focussing.
in FIG. 7, a diagrammatic illustration of the principle of electronic deflection.
in FIG. 8, a diagrammatic illustration of the combination of principles of electronic focussing and deflection.

N the thick sections of these shafts the metallurgical structure is therefore disturbed and remains course, which results in considerable retrodiffusion of the ultrasonic waves. This peculiarity results in the disturbance and attenuation of the transmitting and receiving power of the traditional transducers described above. However, the metallurgical structure is fine on the periphery, where the ultrasonic transmission is satisfactory.

This situation is aggravated when use is made of transducers with transversal waves whose beam necessarily crosses this heterogeneity zone twice for short shafts, i.e. shafts shorter than 2 metres, and even more for long shafts, i.e. shafts up to 3.5 metres long, considering the outward and return trajectories of the ultrasonic beams.

SUMMARY OF THE INVENTION

An object of the present invention is to form an ultrasonic beam outside the metallurgically disturbed zones and to bypass this zone in any testing operation. For this purpose it is proposed in the invention that a non-destructive test to be carried out on a drive shaft that is accessible by only one of the ends with longitudinal waves using an annular multi-element ultrasonic transducer.

Such a transducer includes independent elements that can be excited by electrical pulses of the same frequency, but for which, according to the invention, different electronic phase shifts will be applied to the location of the pulses transmitted to the elements. Such an electronic phase shift enables a final beam, synthesized by all the elements constituting the transducer, to be focussed and deflected, the said final beam being concentrated to adopt a generally cylindrical shape with a cross-section that is much smaller than the cross-section of the shaft to be tested. The final beam is highly energetic at long distance, due mainly to a waveguide effect resulting from the cylindrical geometry of the shaft.

The invention therefore relates essentially to a method of testing a drive shaft of a rotary machine, the said shaft being solid, with a generally cylindrical shape, characterized in that the method comprises the different stages including:

it has, at one end of the shaft to be tested, an annular transducer comprising a plurality of independent elements, each element being capable of at least transmitting an elementary ultrasonic beam of longitudinal waves in the drive shaft;

it applies a predetermined first law of focussing to at least some of the elements constituting the annular transducer, the first law of focussing includes a number of transmission delays to be respected between the different elements of the transducer to generate a first final beam of a generally cylindrical shape deflected at an angle sought to target a first particular sector of the drive shaft to be tested.

The method according to the invention may, as a supplement to the main characteristics that have just been mentioned, have one or more of the following additional characteristics:

the method comprises the additional stage including modifying the first law of focussing to obtain a second law of focussing generating a second final beam to target a second particular sector of the drive shaft to be tested; by thus modifying the first law of focussing, and consequently giving rise to a modification of a deflection of the final beam, it is possible to reach the second sector to be tested located upstream or downstream from the first sector to be tested. Simple electronic management of the delays to be applied therefore provides access to all the zones to be tested;

the method comprises the additional stage including developing the rotation of the annular transducer by means of a motor and about a central axis of the drive shaft;

the method comprises the additional stage including applying the first law of focussing on several occasions by shifting on each occasion, by at least the same number of elements, each delay in the said focussing law;

the annular transducer used in the said method, includes eight independent elements distributed in a single ring;

the method comprises the additional stage including:

applying a first delay to a first element and a second delay to a second element, the second delay being longer than or equal to the first delay;

applying a third delay to a third element, a fourth delay to a fourth element, a fifth delay to a fifth element, a sixth delay to a sixth element, the sixth element being equal to the fifth delay, which is itself longer than the fourth delay, itself equal to the third delay, itself longer than the second delay;

applying a seventh delay to a seventh element, and an eighth delay to an eighth element, the eighth delay being equal to the seventh delay, itself longer than the sixth delay, in order to generate a seventh elementary beam and an eighth elementary beam, concentrated on circular focal point, thereby creating, downstream from the focal point, the final beam which are generally cylindrical in shape;

the first element, the third element, the seventh element and the fifth element are positioned consecutively on a first half of the annular transducer, being symmetrical, in relation to a plane perpendicular to a surface of transmission of the circular transducer and centred on the said transducer, in relation to the second element, the fourth element, the eighth element and the sixth element respectively;

the annular transducer used in the said method comprises a first outer ring, arranged on the periphery of the transducer, and a second inner ring, arranged close to the centre of the transducer, the first and second rings being concentric;

the annular transducer comprises thirty two independent elements, the first and second rings each comprising sixteen elements;

the delays applied to generate two consecutive elementary beams are of the order of one hundredth of a nanosecond;

the sum of the delays constituting all the delays of the first law of focussing is shorter than a duration of transmission of the elementary beam transmitted by each element constituting the annular transducer; and the drive shaft is a wheel shaft of a primary pump of a nuclear reactor.

BRIEF DESCRIPTION OF THE DRAWINGS

The invention and its different applications will be better understood on reading the following description and examining the figures accompanying it. These applications are shown by way of illustration and in no way limit the scope of the invention. The figures show the following.

In the different figures, the elements which are common to several figures will retain the same references, unless otherwise specified.

DETAILED DESCRIPTION

In the method according to the invention the principles of electronic focussing and electronic defection are applied, as shown in FIGS. 6 and 7 respectively, in order to carry out the testing of the condition of a drive shaft.

The principle of electronic focussing, in the example shown in FIG. 6, includes using electronic delays applied in transmission to a plurality of independent elements 600 constituting a rectilinear transducer 601. A law of delay 602—or law of focussing—is applied to a group 604 of independent consecutive elements 600. Generally speaking, the application of a law of delay to a multi-element transducer includes transmitting a single electrical pulse, the said pulse being distributed over several channels, each of the channels terminating in a different element of the transducer considered; each of the channels also has a plurality of means, of the capacitance or inductance type, which enable a delay peculiar to it at the output of the channel considered.

The law of delay 602 includes transmitting initially the ultrasonic beams of the elements located on the periphery of group 604 of independent elements shown. Delays are then applied to the other independent elements of group 604; the delay applied to each independent element is an ascending function of the distance of the element considered from the periphery of group 604 of independent elements shown: the more the independent group occupies a central position, the greater the delay applied to it. A focal point 603, located at a focal length D from transducer 601 considered, is therefore obtained. Focal length D depends essentially on the amplitude of the law of delay 602.

The principle of electronic deflection, in the example shown in FIG. 7, is again illustrated with reference to the plurality of independent elements 600 constituting rectilinear transducer 601. Here again electronic delays are applied, in transmission to group 604 shown of consecutive independent elements 600. A law of delay 700 is applied, including initially transmitting the ultrasonic beam of the element located at one of the ends of group 604, the right end in the example considered. Delays are then applied to the other independent elements of group 604; the delay applied to each independent element is an ascending function of the distance of the element considered from the element to which the first electrical pulse has been applied: the more the independent element occupies a position that is distant from the first element excited by an electrical pulse, the longer the delay applied to it. A global beam is therefore obtained that is deflected in a direction corresponding to the position of the last element that has transmitted an ultrasonic beam.

Henceforth in the description the term focussing law generally refers to a plurality of delays to be applied to different elements of a transducer, the said delays making their contribution either in deflection, in focussing or in deflection and focussing on the final beam generated by the transducer.

FIG. 8 illustrates the fact that a combination of the principles of electronic focussing and electronic deflection, based on an appropriate law of focussing 80, enables an ultrasonic beam 801 to be obtained that is synthesized by group 604 of consecutive independent elements 600 of rectilinear transducer 603, shown in FIG. 6, by virtue of the principle of electronic deflection.

Figure 9:
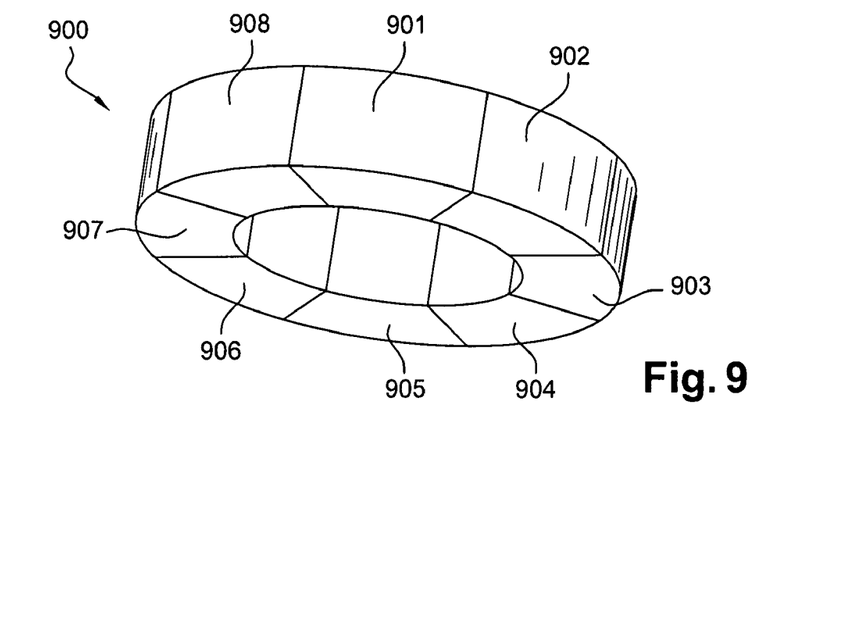
in FIG. 9, a first simplified embodiment of the transducer used in an application of the method according to the invention.

In order to implement the method according to the invention it is proposed to apply the principles of electronic focussing and electronic deflection that have just been described to a multi-element annular transducer, the first simplified embodiment 900 of which is shown in FIG. 9. Transducer 900 includes eight consecutive independent elements regularly distributed throughout the volume constituting the transducer, references 901 to 908 respectively. Such a transducer makes it possible, in particular, to generate a final beam 1100, shown in FIG. 11, that is generally cylindrical in shape.

Figure 11:
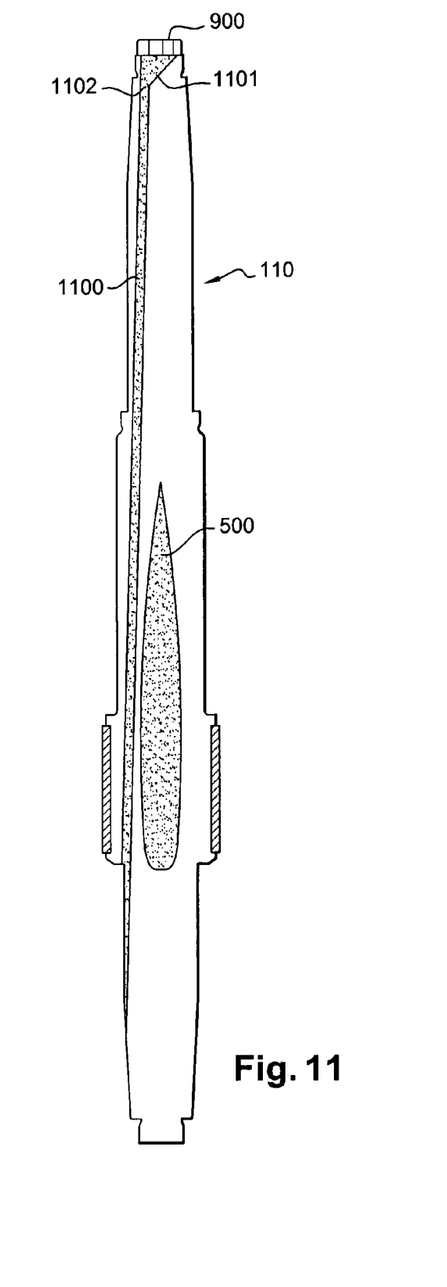
in FIG. 11, a diagrammatic representation of an application of the method according to the invention within the framework of a static test.

To obtain such a beam it is possible, for example, to apply a law of focussing comparable to the law of focussing 800 in FIG. 8; such a law of focussing is related to four first consecutive elements of the transducer, the said first four elements constituting a first half of the transducer; the same law of focussing is simultaneously applied to four last consecutive elements of the transducer symmetrical to the four first elements of the transducer. Such an example of a law of focussing therefore includes transmitting the elementary ultrasonic beams associated with each element 901 to 908, respecting the following orders of transmission:

in a first time, simultaneously or almost exciting (i.e. with an excitation delay shorter than 100 ns (nanoseconds)) element 901 and element 908; the elementary beams thus produced are used mainly to obtain a deflection of the final beam synthesized in a direction 1101;

in a second time, simultaneously or almost exciting elements 902 and 907, then elements 904 and 905; the elementary beams thus produced also contribute to the deflection of the final synthesised beam and to obtaining a focal point 1102 that is generally circular;

finally, in a third time, simultaneously or almost exciting elements 903 and 906. The elementary beams generated by these last two elements will then be physically concentrated on focal point 1102 because of the energy volume of the adjoining space due to the elementary ultrasonic beams which begin to be transmitted before elements 903 and 906, but are still being transmitted when the elementary beams associated with elements 903 and 906 are being transmitted. Concentrated in this manner from their production in elements 903 and 906, the elementary beams produced by these two elements are capable of being deeply diffused in drive shaft 110; the shape they adopt beyond focal point 1102 is generally cylindrical due to the generally cylindrical shape of shaft 110 in which they are projected, this cylindrical shape of the shaft preventing these elementary beams from diverging. Such a phenomenon is known by the name of the cylinder effect.

Figure 10:
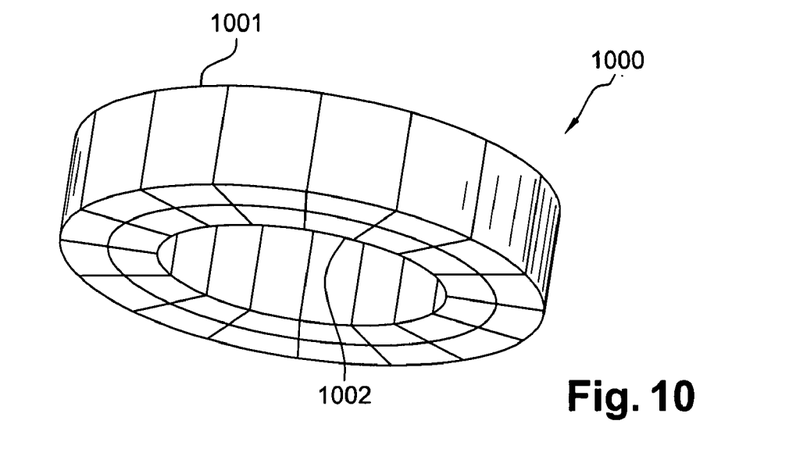
in FIG. 10, a second embodiment of the transducer used in an application of the method according to the invention.

FIG. 10 shows a second embodiment 1000 of an annular transducer used in certain implementations of the method according to the invention. Transducer 1000 includes thirty two independent elements distributed in two concentric rings: a first ring 1001, comprising 16 elements, constitutes the periphery of transducer 1000. Its function is to generate an intermediate ultrasonic beam within which will be synthesized the final ultrasonic beam, produced by a second ring 1002 also comprising 16 elements and located near the centre of annular transducer 100. The intermediate ultrasonic beam then serves mainly to compensate for the variations in cross-section of the shaft to be tested; in fact, such variations in cross-section may, at their level, cause slight deformations of the final synthesized beam, thus rendering the latter less cylindrical. In order to perfect the cylindrical shape of the final beam, provision is therefore made for the production of an intermediate beam that has a central hollow, cylindrical section, thus ensuring that the final beam benefits more from the cylinder effect.

In the method according to the invention ultrasonic beams may therefore be generated which are:

deflected at a predetermined angle, the angle adopted by the final beam depending essentially, referring to the first embodiment of transducer 900, on the delay applied between elements 901 and 908 and the other elements. The defection may therefore be modulated on demand so that the entire lower section of the shaft can be probed with the same transducer by partial modification of the electronic delays of the focussing law;

of a constant cross-section and having a diameter that is less than one third of the diameter of that section of the shaft that contains the zone to be tested, which confers upon the final beam a high long-distance energy density by taking advantage of the cylindrical geometry of the shaft.

In the invention the delays applied to the different elements constituting the transducer used to generate a given final beam are generally such that their sum is less than the time during which each of the said elements transmits its elementary beam; the final beam obtained, with a generally cylindrical shape, is therefore the resultant of a spatial coexistence of all the elementary beams fired and transmitted by all the elements constituting the transducer, the different shots having been initiated by respecting the delays dictated by the focussing law applied.

The loss of energy between the outward trajectory and return of the final beam is minimal because the latter avoids the zone of heterogeneities 500 present in the central section of shaft 110; the small cross-section of the final beam relative to the diameter of the tested zones provides a good resolution of the size and shape of the defect, as well as precise location by gradual rotation of the sensor on it. For reasons of the high energy density of the final synthesized beam, the incident energy also enables the presence of axial cracks to be detected by diffraction. In other words, the cylindrical ultrasonic beam obtained by the method of the invention is highly energetic over a long distance, which makes it possible to operate not only in wave reflection but also in diffraction on the defects observed of the crack opening type.

Figure 12:
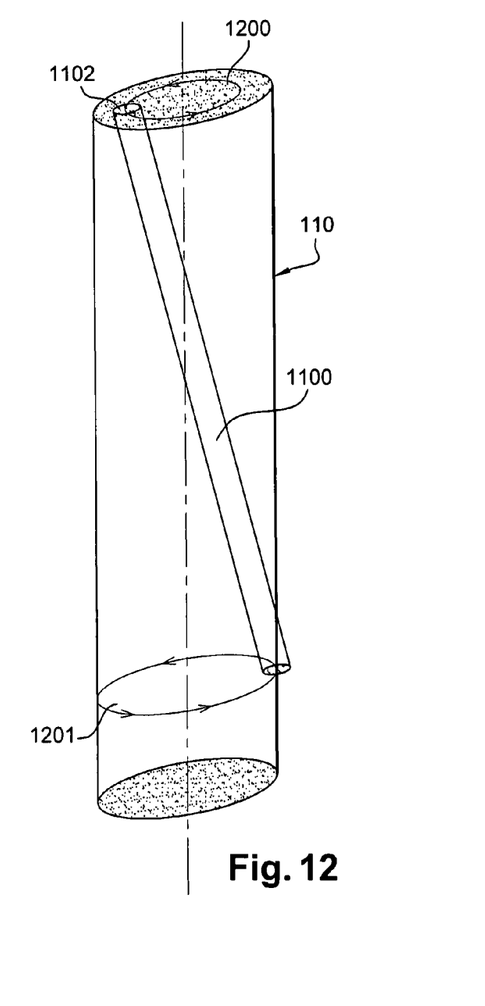
in FIG. 12, a diagrammatic representation of an application of the method according to the invention within the framework of a dynamic test.

In a first embodiment of the method according to the invention the relative delays between the transmission pulses applied to each of the elements represent a fixed, static law of focussing. As shown in FIG. 12, transducer 900 is driven by mechanical rotation 1200 on itself, for example by means of a rotary drive device of the motor type, not shown, in order to scan a periphery 1201 of the zone of shaft 110 at the desired distance.

In a second embodiment of the method according to the invention, the mechanical rotation may be replaced by keeping transducer 900 immobile at the accessible end of the shaft to be tested by circular electronic scanning applied successively to the different elements; such an implementation may be considered of interest, particularly if the ambient space available does not permit the use of the rotary drive device. However, such an implementation only permits an angular precision to be obtained that is not as fine as that available with the first embodiment.

The current requirements relate to forged stainless steel shafts up to 3.5 metres long and 0.4 m in diameter. If necessary, the transducers used in the method according to the invention may be adapted for testing larger parts.

What is claimed is:

1. A method for testing a drive shaft of a rotary machine, the drive shaft being solid, of a generally cylindrical shape, the method comprising the steps of:
providing, at one end of the shaft to be tested, an annular transducer including a plurality of independent elements, each element being capable of at least transmitting an ultrasonic elementary beam in longitudinal waves in the drive shaft; and
applying a first predetermined law of focussing to at least some of the independent elements, the first law of focussing including a number of transmission delays to be respected between the different elements of the transducer, in order to generate a first final beam having a generally cylindrical shape and deflected at a predetermined angle in order to target a first particular sector of the drive shaft to be tested.

2. The method according to claim 1, further comprising modifying the first law of focussing in order to obtain a second law of focussing generating a second final beam in order to target a second particular sector of the drive shaft to be tested.

3. The method according to claim 1, further comprising rotating the annular transducer using a motor and about a central axis of the drive shaft.

4. The method according to claim 1, further comprising applying the first law of focussing on several occasions by shifting, on each occasion, by at least the same number of the individual elements, each delay.

5. The method according to claim 1, wherein the annular transducer includes eight of the independent elements distributed in a single ring.

6. The method according to claim 5, further comprising:
applying a first delay to a first element of the independent elements and a second delay to a second element, the second delay being longer than or equal to the first delay;
applying a third delay to a third element, a fourth delay to a fourth element, a fifth delay to a fifth element, a sixth delay to a sixth element, the sixth delay being equal to the fifth delay, itself longer than the fourth delay, itself equal to the third delay, itself longer than the second delay;
applying a seventh delay to a seventh element, and an eighth delay to an eighth element, the eighth delay being equal to the seventh delay, itself longer than the sixth delay, in order to generate a seventh elementary beam and an eighth elementary beam, concentrated on a circular focal point, thereby creating, downstream from the focal point, the first final beam.

7. The method according to claim 6, wherein the first element, the third element, the seventh element and the fifth element are located consecutively on a first half of the annular transducer, these elements being symmetrical, in relation to a plane perpendicular to a transmission surface of the circular annular transducer and centered on the transducer, to the second element, the fourth element, the eighth element and the sixth element respectively.

8. The method according to claim 1, wherein the annular transducer includes a first outer ring, arranged on a periphery of the transducer, and a second inner ring, arranged closer to the center of the transducer, the first and second rings being concentric.

9. The method according to claim 8, wherein the annular transducer includes thirty two of the independent elements, the first and second rings each comprising sixteen of the independent elements.

10. The method according to claim 1, wherein the delays applied to generate two consecutive elementary beams are of the order of one hundred of a nanoseconds.

11. The method according to claim 1, wherein a sum of the delays constituting all the delays of the first law of focussing is shorter than a transmission time of the elementary beam transmitted by each independent element of the annular transducer.

12. The method according to claim 1, wherein the drive shaft is a wheel shaft of a primary pump of a nuclear reactor.

* * * * *